United States Patent
Chuang

(10) Patent No.: US 7,425,650 B1
(45) Date of Patent: Sep. 16, 2008

(54) SYNTHESIS OF ASYMMETRIC TETRACARBOXYLIC ACIDS AND CORRESPONDING DIANHYDRIDES

(75) Inventor: Chun-Hua Chuang, Brecksville, OH (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 49 days.

(21) Appl. No.: 11/378,553

(22) Filed: Mar. 18, 2006

Related U.S. Application Data

(63) Continuation-in-part of application No. 10/897,279, filed on Jul. 23, 2004, now Pat. No. 7,015,304.

(51) Int. Cl.
*C07C 63/00* (2006.01)
*C07C 63/33* (2006.01)
*C07C 53/00* (2006.01)

(52) U.S. Cl. .................. 562/488; 562/491; 562/480; 562/887

(58) Field of Classification Search ................ None
See application file for complete search history.

(56) References Cited

U.S. PATENT DOCUMENTS

| | | | |
|---|---|---|---|
| 3,940,426 A | 2/1976 | Itatani | 528/353 |
| 4,294,976 A | 10/1981 | Itatani | 560/76 |
| 4,958,002 A | 9/1990 | Imatani | 528/353 |
| 5,258,530 A | 11/1993 | Katsuro | 549/241 |
| 2003/0088120 A1 | 5/2003 | Yamamoto | 560/76 |

FOREIGN PATENT DOCUMENTS

EP 343560 * 11/1989

OTHER PUBLICATIONS

Polyhedron, 10(17), 2037-44; 1991.*

* cited by examiner

*Primary Examiner*—Karl J Puttlitz
(74) *Attorney, Agent, or Firm*—Kent N. Stone; James V. Tura

(57) ABSTRACT

This invention relates to processes for preparing asymmetrical biphenyl tetracarboxylic acids and the corresponding asymmetrical dianhydrides, namely 2,3,3',4'-biphenyl dianhydride (a-BPDA), 2,3,3',4'-benzophenone dianhydride (a-BTDA) and 3,4'-methylenediphthalic anhydride (-MDPA). By cross-coupling reactions of reactive metal substituted o-xylenes or by cross-coupling o-xylene derivatives in the presence of catalysts, this invention specifically produces asymmetrical biphenyl intermediates that are subsequently oxidized or hydrolyzed and oxidized to provide asymmetric biphenyl tetracarboxylic acids in comparatively high yields. These asymmetrical biphenyl tetracarboxylic acids are subsequently converted to the corresponding asymmetrical dianhydrides without contamination by symmetrical biphenyl dianhydrides.

30 Claims, No Drawings

_US 7,425,650 B1_

SYNTHESIS OF ASYMMETRIC TETRACARBOXYLIC ACIDS AND CORRESPONDING DIANHYDRIDES

RELATED U.S. APPLICATION

This application is a continuation-in-part of application Ser. No. 10/897,279 filed Jul. 23, 2004 now U.S. Pat. No. 7,015,304.

ORIGIN OF INVENTION

The invention described herein was made by an employee of the United States Government and may be manufactured and used by or for the Government for governmental purposes without the payment of any royalties thereon or therefor.

FIELD OF THE INVENTION

This invention relates to the synthesis of a series of asymmetric tetracarboxylic acids and the corresponding dianhydrides, namely, 2,3,3',4'-biphenyldianhydride (a-BPDA), 2,3,3',4'-benzophenone dianhydride (a-BTDA), and 3,4'-methylenediphthalic anhydride (a-MDPA). These tetracarboxylic acids and corresponding dianhydrides were prepared by cross-coupling of two asymmetrical-substituted o-xylenes or corresponding derivatives (Suzuki coupling) with various catalysts to form tetracarboxylic acids and the corresponding 2,3,3',4'-tetramethylbiphenyl and 2,3,3',4'-tetramethylbenzophenone. The asymmetrical tetramethylbiphenyl and the tetramethylbenzophenone were oxidized to obtain the corresponding tetracarboxylic acids which were then converted to 2,3,3',4'-a-biphenyl dianhydride and 2,3,3',4'-a-benzophenone dianhydride. In addition, the benzophenone tetracarboxylic acid can be reduced by hydrzine hydrate to 3,4'-methylene diphthalic tetracarboxylic acids which is converted to the corresponding 3,4'-methylenediphthalic anhydride. The unique feature of this invention is that it allows the production of a series of asymmetric dianhydrides, not only a-BPDA, but also a-BTDA and a-MDPA. This capability of producing a-BPDA, a-BTDA and a-MDPA, will usher in innovation for the preparation of high $T_g$, low-melt viscosities and colorless polyimides with interesting and novel properties for aerospace and electronic applications.

Thermosetting polyimides derived from 2,3,3',4'-a-biphenyl dianhydride (a-BPDA) has been shown to provide high $T_g$ polyimides for resin transfer molding; see the Proceedings of the SAMPE Symposium, Long Beach, Calif., May 1-5, 2005. Recently, it was discovered that asymmetric 2,3,3',4'-biphenyl dianhydride (a-BPDA) reacted with diamines and an endcap produces polyimides with lower-melt viscosities and higher glass transition temperatures ($T_g$) than the symmetrical 3,3',4,4'-biphenyl dianhydride (s-BPDA); see High Performance Polymers, Vol. 13, 355 (2001), and Vol 15, 375 (2003).

BACKGROUND OF THE INVENTION

Currently, asymmetrical a-BPDA is being prepared from o-xylene or o-phthalate via an oxidative coupling reaction, which essentially yields a mixture of 3,3',4,4'-biphenyl dianhydride (s-BPDA) and a minor product (2-6%) of a-BPDA. Consequently, a-BPDA is being produced in limited quantity and therefore is not commercially available in sufficient amounts, despite an enormous interest in preparing polyimides using a-BPDA. This invention discloses alternative and more efficient processes for exclusively producing asymmetric 2,3,3',4'-biphenyl dianhydride (a-BPDA), 2,3,3',4'-benzophenone dianhydride (a-BTDA) and 3,4'-methylendiphthalic anhydride (a-MDPA). The asymmetric 2,3,3',4'-biphenyl dianhydride (a-BPDA) has received more attention, because this dianhydride can produce polyimide resins having low-melt viscosities and higher glass-transition temperatures ($T_g$) than the symmetrical 3,3',4,4'-biphenyl dianhydride (s-BPDA).

The prior art (U.S. Pat. No. 3,940,426, UBE Industries) process for making a-BPDA relies on oxidative coupling of o-xylene or methyl o-phthalate with an organic acid salt of palladium under oxygen pressure to produce symmetrical and unsymmetrical intermediates which are oxidized and cyclodehydrated to form a mixture of a-BPDA and s-BPDA. This mixture requires the additional process of separating the two isomers.

U.S. Pat. No. 4,294,976 discloses a process for preparing a mixture of biphenyltetracarboxylic acids (3,3',4,4'-isomer, 2,3,3',4'-isomer and 2,2',3,3' isomer) via an oxidative coupling of either o-xylene or o-phthalate in the presence palladium catalyst, followed by hydrolysis. The mixture of isomeric biphenyltetracarboxylic acids were then subjected to fractionally recrystallization to obtain each of the corresponding 2,3,3',4'-(minor amount) and 3,3',4,4'-(major amount) and minute amount of 2,2',3,3'-biphenyldianhydrides.

U.S. Pat. No. 4,958,002 teaches a dehydration process to obtain 3,3',4,4'-biphenyl dianhydride after the corresponding 3,3',4,4'-biphenyltetracarboxylic acid was isolated from 2,3,3',4'-biphenyltetracarboxylic acid. U.S. Pat. No. 5,258,530 (Mitsibishi) describes a coupling reaction of phthalic anhydride directly to a mixture of 2,3,3',4'-(major) and 2,3,3',4'-(minor) biphenyl dianhydrides. U.S. Patent Publication No. 0088120 A1 (2003) discloses a process for producting predominately 2,3,3',4'-biphenyl dianhydride (a-BPDA) over a minor amount of 3,3',4,4'-biphenyldianhydride (s-BPDA) using a palladium and copper catalyst along with bidentate ligand. These prior art processes yield mixtures of asymmetrical 2,3,3',4'-BPDA together with symmetrical 3,3',4,4'-BPDA, which then requires the separation of these isomers. In comparison, this invention discloses an asymmetrical coupling of substituted o-xylenes to provide asymmetrical 2,3,3',4'-BPDA exclusively without a mixture or contamination by the symmetrical 3,3',4,4'-BPDA or 2,2',3,3'-BPDA.

SUMMARY OF THE INVENTION

By employing a cross-coupling reaction (Suzuki coupling) with 3- and 4-substituted o-xylenes in the presence of catalyst, this invention exclusively produces asymmetric precursors; namely, 2,3,3',4'-tetramethylbiphenyl and 2,3',3',4'-tetramethylbenzophenone. These asymmetric precursors are oxidized or hydrolyzed and oxidized to produce the corresponding asymmetric tetracarboxylic acids and subsequently converted to the corresponding dianhydrides (a-BPDA, a-BTDA, and a-MDPA) in reasonable high yields.

The dianhydrides of this invention are useful particularly in preparing polyimides which comprise an important class of polymers because of their desirable characteristics i.e. low dielectric constant, high breakdown voltage, good wear resistance, radiation resistance, inertness to solvents, good adhesion properties, hydrolytic stability, low thermal expansion, long-term stability, and excellent mechanical properties. Specifically, high temperature polyimides, such as PMR-15, are extremely valuable particularly for aerospace applications. However, making components from these polymers via prepreg process is labor intensive and expensive. Resin Transfer Molding (RTM) is a cost-effective approach to making components and has been successfully deployed with low-temperature polymers. U.S. Pat. No. 7,015,304 discloses preparation of polyimides with melt viscosities sufficiently low to enable RTM processing while maintaining stability and high temperature properties.

Accordingly, it is an object of this invention to provide processes for cross-coupling 3- and 4-substituted o-xylenes and corresponding derivatives to produce asymmetric precursors which are subsequently oxidized to tetracarboxylic acids and then converted to the corresponding dianhydrides.

It is another object of this invention to provide processes for preparing asymmetrical tetracarboxylic acids and the corresponding dianhydrides useful in producing polyimides having lower-melt viscosities and high glass transition temperatures ($T_g$).

It is a further object of this invention to provide processes for the synthesis of a-BPDA and two additional dianhydrides a-BTDA and a-MDPA by cross-coupling substituted o-xylenes to produce asymmetric precursors which are subsequently oxidized to the corresponding tetracarboxylic acids and then converted to the corresponding asymmetric dianhydrides in comparatively high yields.

These and other objects of this invention will become apparent from a further and more detailed description of the processes.

DETAILED DESCRIPTION OF THE PREFERRED EMBODIMENTS

Recently, asymmetric 2,3,3',4'-biphenyl dianhydride (a-BPDA) has received more attention, because it can be used to produce polyimide resins having low-melt viscosities and high glass transition temperatures in comparison to the symmetrical 3,3',4,4'-biphenyl dianhydride (s-BPDA). In comparison, the prior art discloses a process for preparing a-BPDA by oxidative coupling of o-xylene or methyl o-phthalate with an organic acid salt of palladium under oxygen pressure to produce symmetrical and unsymmetrical intermediates which are oxidized and cyclodehydrated to obtain a mixture of a-BPDA and s-BPDA, followed by a process of which requires separating the two isomers.

The present invention exclusively provides processes for preparing asymmetrical tetracarboxylic acids and the corresponding dianhydrides, namely 2,3,3',4'-biphenyl dianhydride (a-BPDA), 2,3,3',4'-benzophenone dianhydride, (a-BTDA and 3,4'-methylenediphthalic anhydride (-MDPA), without the complex process of separating the isomers. By employing the cross-coupling of reactive metals such as magnesium (Mg), zinc (Zn) or lithium (Li) [Scheme I] as well as the cross-reaction (Suzuki coupling) as shown in Scheme II and Scheme III using catalysts, alone or with co-catalysts or co-ligands, this invention specifically produces asymmetrical biphenyl intermediates that are subsequently hydrolyzed and oxidized or only oxidized to the asymmetric biphenyl tetracarboxylic acids. These asymmetrical biphenyl tetracarboxylic acids are converted to the corresponding asymmetrical dianhydrides either through cyclodehydration thermally or in the presence of an anhydride, without contamination of any symmetrical dianhydrides.

Scheme I of this invention illustrates the synthetic route via the active metal coupling of either substituted o-xylene (A) or 4-halophthalic anhydride or 4-halophthalimide (B) to afford the coupled intermediates of (D) and (E), which are oxidized or hydrolyzed and oxidized to form the tetracarboxylic acid (F), followed by dehydration e.g. with acetic anhydride to obtain the corresponding asymmetrical dianhydrides (G), which corresponds to 2,3,3',4'-biphenyl dianhydride (a-BPDA) when R is nil, and 3,4'-methylenediphthalic anhydride (a-MDPA) when R is $CH_2$.

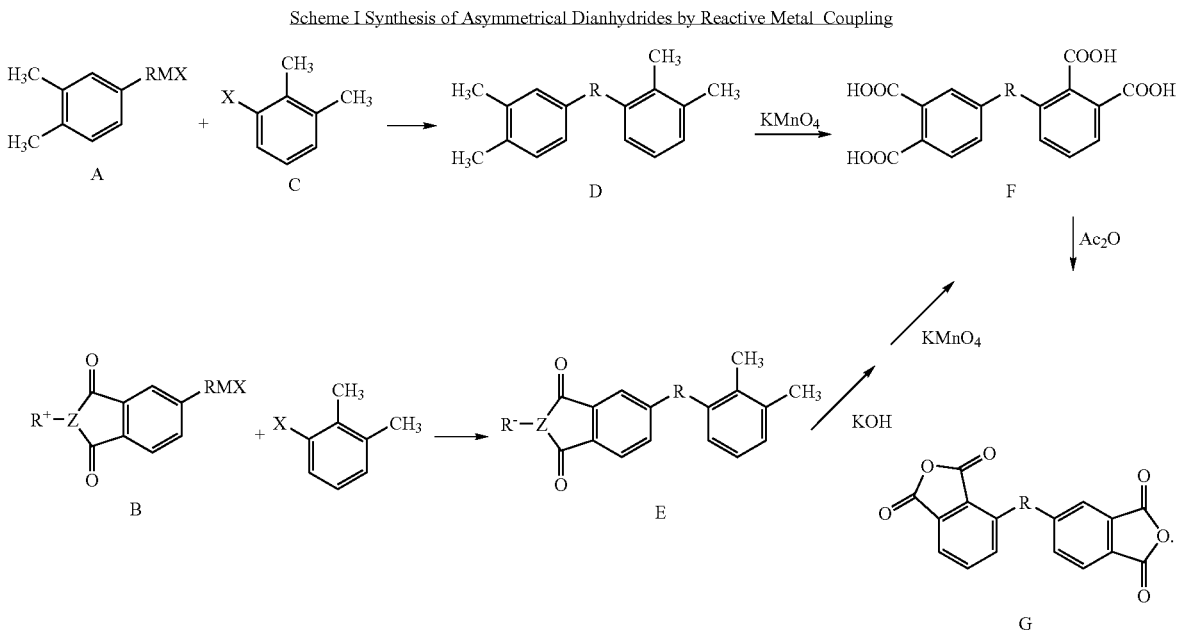

As shown in the reactions of Scheme II, the asymmetric dianhydrides are obtained by cross-coupling o-xylene derivatives (I) and (II), if (I) is a 3-boron substituted o-xylene, then (II) is a 4-substituted o-xylene, or if (I) is a 4-boron substituted o-xylene, then (II) is a 3-substituted o-xylene derivative.

2,3,3',4'-biphenyl dianhydride (a-BPDA) is prepared by cross-coupling (1) and (II), where X is selected from the group consisting of Cl, Br, I, OSO$_2$CF$_3$, OSO$_2$CH$_3$ and Y is (OH)$_2$, or (OR)$_2$, where R is a lower alkyl group such as CH$_3$, C$_2$H$_5$, i-Pr, in order to form the asymmetrical 2,3,3',4'-tetramethylbiphenyl (III) in a common organic solvent, e.g. toluene, N,N-dimethylormamide (DMF), dimethoxyethane (DME), 1,4-dioxane, tetrahydrofuran (THF), anisole, or aqueous solution with phase transfer catalysts in the presence of palladium or nickel catalysts, either with or without a co-catalysts or co-ligands, such as Pd (PPh$_3$)$_4$, Pd(OAc)$_2$, Pd (PPh$_3$)$_2$Cl$_2$, PdCl$_2$(CH$_3$CN)$_2$, Pd(dba)$_2$/P(t-Bu)$_3$, Pd$_2$(dba)$_2$/[t-Bu)$_2$PH]BF$_4$, NiCl$_2$ (PPh$_3$)$_2$, NiCl$_2$(PCy$_3$)$_2$, NiCl$_2$(dppf), NiCl$_2$(dppe), NiCl$_2$(dppb), and their corresponding polymer bound palladium or nickel catalysts.

Compound (III) is oxidized by potassium permanganate (KMnO$_4$), chromium trioxide (CrO$_3$), or by other oxidation methods such as low or high pressure nitric acid oxidation or by oxygen to form the 2,3,3',4'-biphenyltetracarboxylic acid (IV), which upon dehydration e.g. by acetic anhydride or thermal dehydration, yields 2,3,3',4'-biphenyl dianhydride (V). Alternatively, compounds (I) and (II) are cross-coupled with carbon monoxide gas in the presence of the Pd or nickel catalysts to form the asymmetrical 2,3,3',4'-tetmmethylbenzophenone (VI), which is further oxidized e.g. by KMnO$_4$, CrO$_3$, low pressure nitric acid with oxygen, or with other known oxidation method to form 2,3,3',4'-benzophenonetetracarboxylic acid (VII) which is then dehydrated by acetic anhydride or thermally cyclodehydrated to yield 2,3,3',4'-benzophenone dianhydride (VII). Alternatively, 2,3,3',4'-benzophenonetetracarboxylic acid (VIII) is reduced by hydrazine to form 3,4'-methylenediphthalic acid (IX), which upon dehydration e.g. by acetic anhydride yields 3,4'-methylenediphthalic anhydride (X).

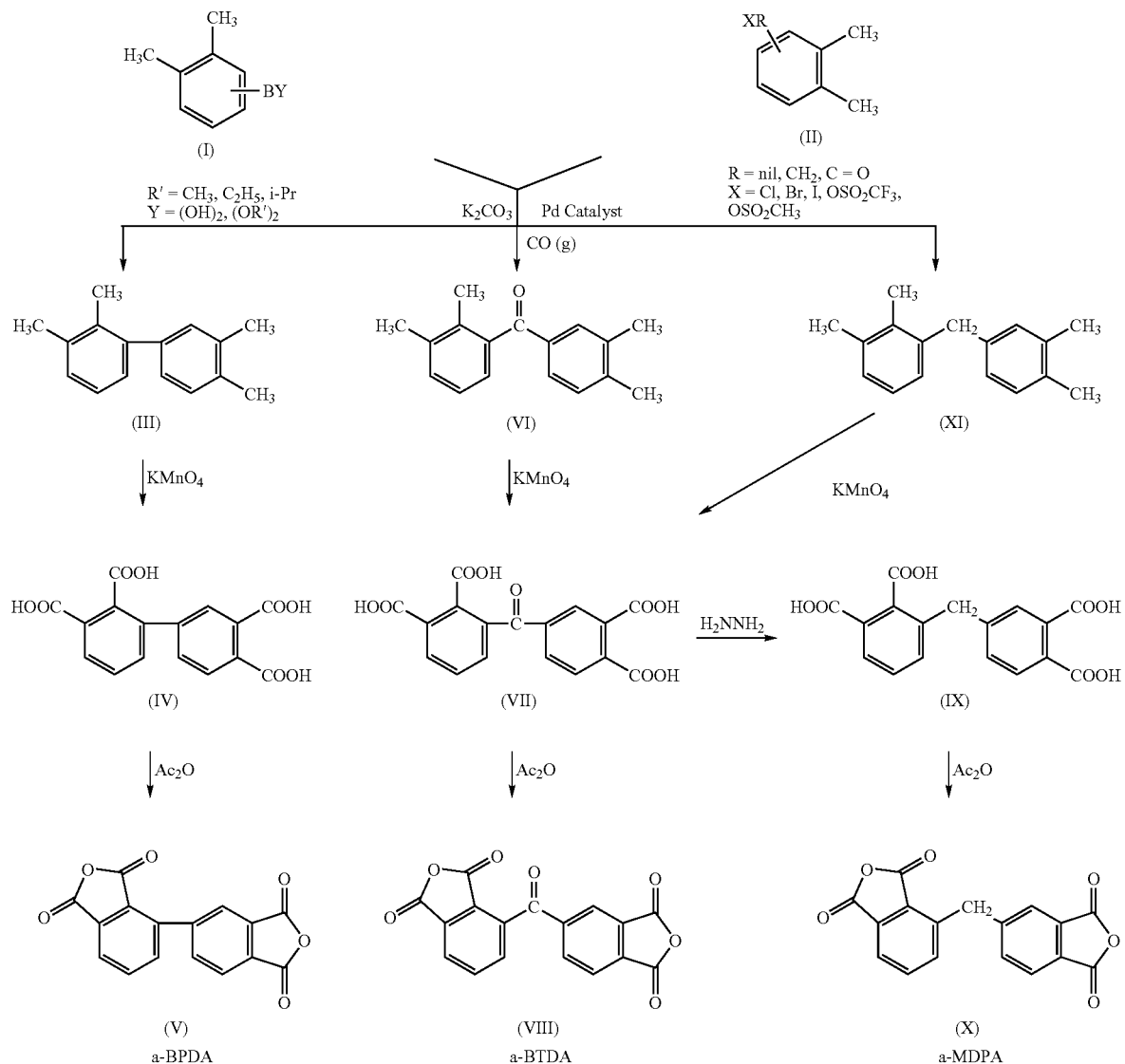

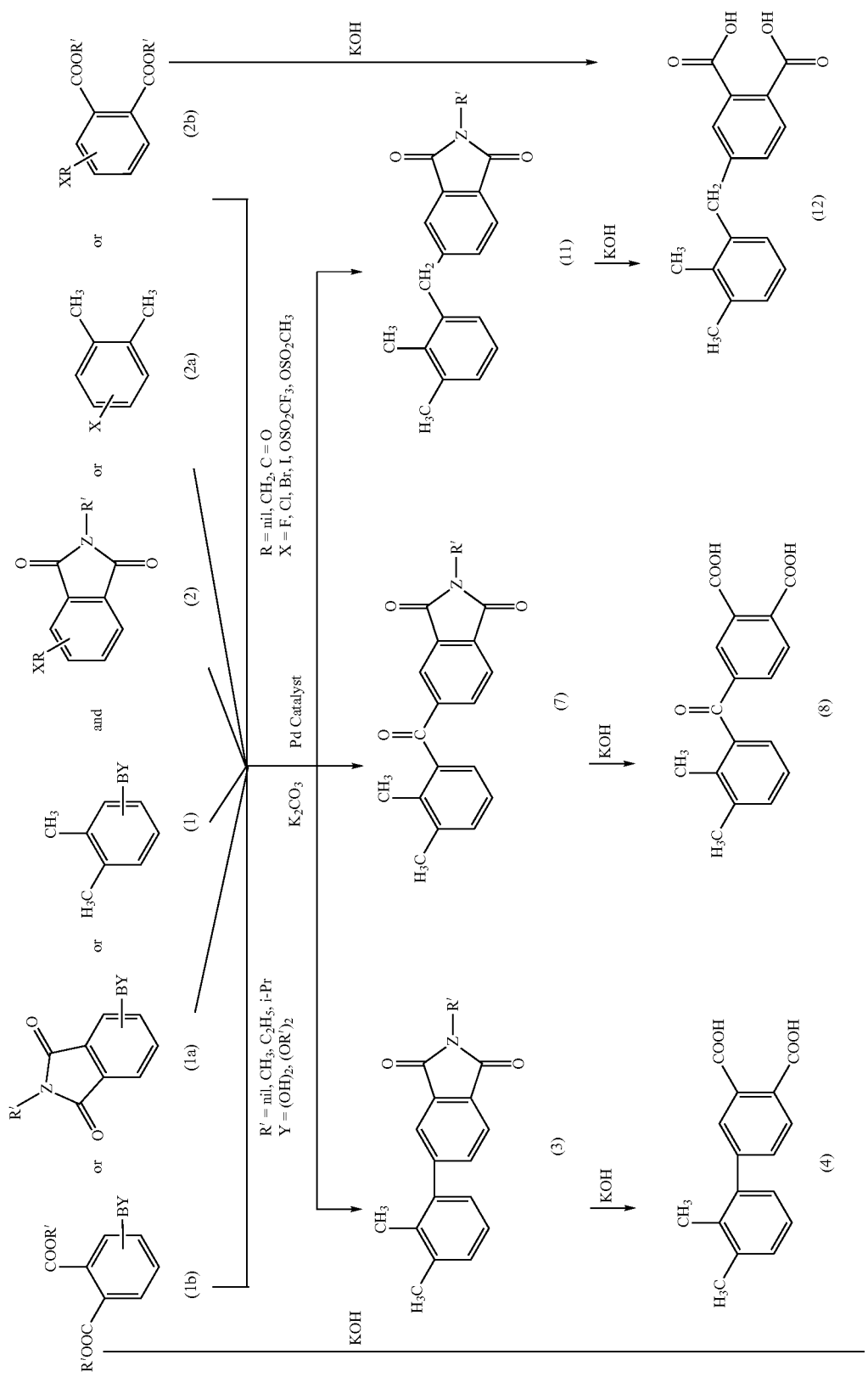

-continued
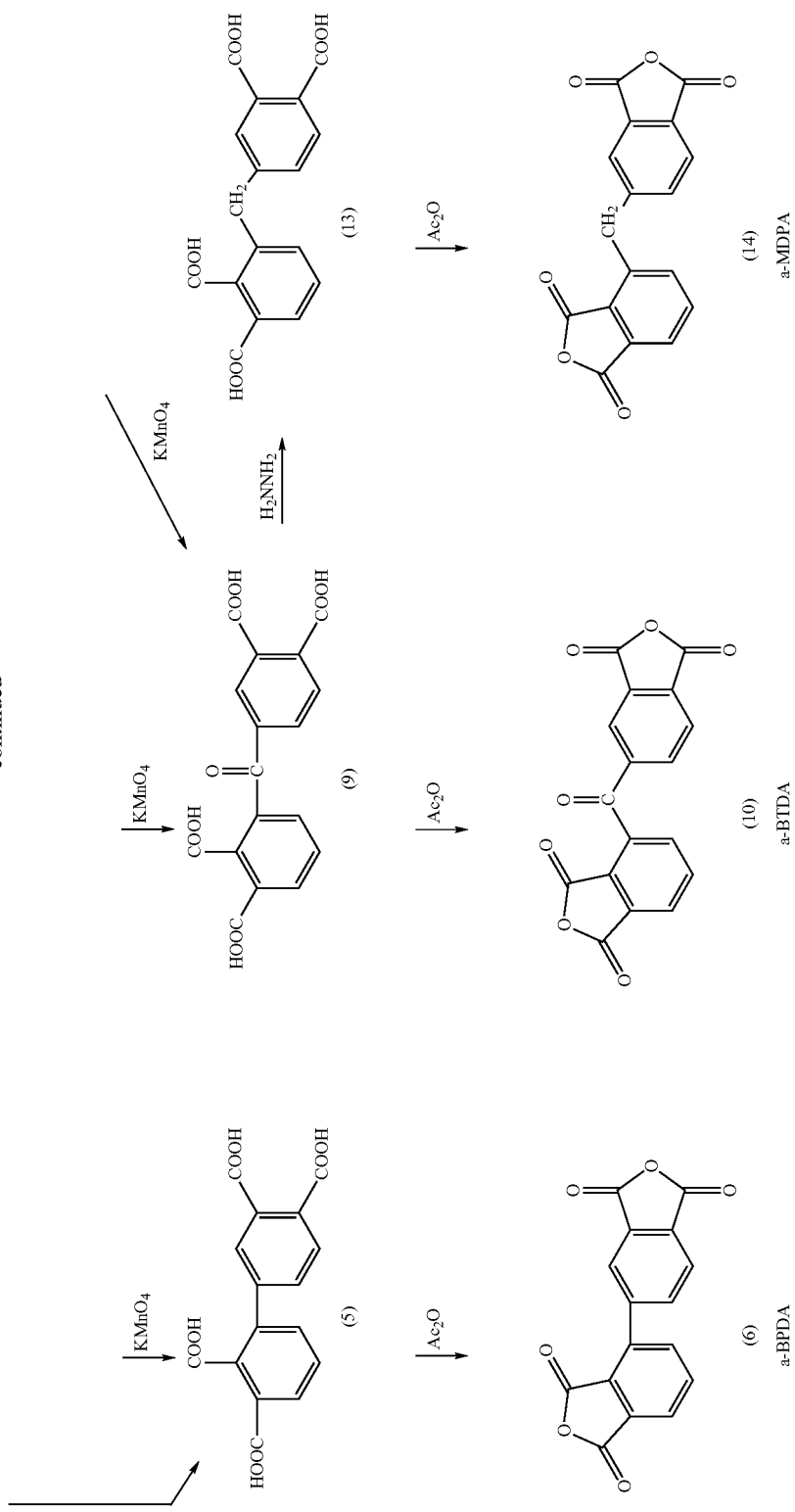

In Scheme III, using catalysts described in Scheme II, a similar Suzuki cross-coupling reaction is carried out between 3- or 4-substituted boron-substituted o-xylene (1), boron-substituted phthalic derivative (1a) or boron-substituted phthalic diester (1b), and 4- or 3-halo-substituted phthalic anhydrides or phthalimides (2), or diesters of phthalic acid respectively, to produce the coupled asymmetrical 4-(2,3-dimethylphenyl)phthalic anhydride or phthalimide (3). Compound (3) can be hydrolyzed e.g. by potassium hydroxide, followed by oxidation e.g. by KMnO$_4$, CrO$_3$ and other oxidizing methods such as low or high pressure nitric acid or with oxygen, to afford 2,3,3',4'-biphenyl tetracarboxylic acid (5), which upon dehydration e.g. with acetic anhydride or thermal cyclodehydration to yield 2,3,3',4'-biphenyl dianhydride (a-BPDA). In the presence of carbon monoxide gas, 2,3,3',4'-benzophenone dianhydride (10), (a-BTDA) is produced by similar routes from compounds (1) and (2) via compounds (7), (8) and (9) as shown in this reaction. Alternatively, 2,3,3',4'-benzophenonetetracarboxylic acid (9) is obtained through KMnO$_4$ oxidation of (2,3-dimethylphenyl)-α-methylphthalic acid (12) after hydrolysis or from the corresponding phthalimide (11) via the Suzuki coupling of an o-xylene derivative (1) with α-halomethylphthalic anhydride or α-halomethylphthalimide (2) with palladium or nickel catalysts. 2,3,3',4'-benzophenone tetracarboxylic acid (9) can be reduced by hydrazine to 3,4'-methylene diphthalic acid (13), which upon dehydration yields 3,4'-methylene diphthalic anhydride (14) (a-MDPA).

In the cross-coupling reactions, X is selected from the group consisting of a halogen e.g. Cl, F, Br, I, or OSO$_2$CF$_3$ and OSO$_2$CH$_3$. Y is either (OH)$_2$, or (OR)$_2$. Z is either oxygen or nitrogen. R is —CH$_2$, —C=O, or nil. R' is a lower alkyl such as CH$_3$, or C$_2$Hs, and B is boron.

The following example illustrates a process for preparing the tetracarboxylic acids and corresponding dianhydrides using a process of this invention.

EXAMPLE I

Synthesis of 4-(2,3-Dimethylphenyl)-N-methylphthalimide[1,2] (3)

To a 250 ml 3-necked flask equipped with mechanical stirrer, 2,3-dimethylphenylboronic acid (10 g, 66.7 mmol) 4-bromo-N-phenylphthalimide (2) (14.4 gm, 60 mmol), potassium carbonate (24.78 g, 180 mmol), a selected palladium catalyst (1.89 mmol) were added, along with 200 ml of dry dioxane. The heterogeneous reaction mixture was heated to 80-85° C. under nitrogen overnight. The reaction mixture was filtered warm to remove any potassium carbonate and potassium fluoride. The dioxane layer was evaporated to dryness to afford 10 g of the product.

Synthesis of 4-(2,3-dimethylphenyl)phthalic acid (4)

To a 3-necked flask equipped with mechanical stirrer, 4-(2,3-dimethyl)-N-phenylphthalimide (3) (13.25 gm, 50 mmol), potassium hydroxide (10 gm, 180 mmol) were added along with 60 ml of water. Additional 15 ml of 95% ethanol was added to prevent the sublimation of (3) during heating. The heterogeneous reaction mixture was heated to reflux until it becomes homogeneous overnight, and then all of the ethanol was distilled off via a Dean-Stark trap. The aqueous reaction mixture was heated to reflux for one more day until the hydrolysis was completed to form 4-(2,3-dimethyphenyl)phthalic acid. The solution was cooled and then acidified with concentrated 30% hydrochloric acid and an oil suspension was formed in the aqueous solution. The heterogeneous reaction mixture was extracted with ethyl acetate, dried over anhydrous magnesium sulfate, and then concentrated to induce crystallization of the desired product (8.1 gm, 60%).

Synthesis of 2,3,3',4'-Biphenyltetracaroboylic acid (5)

To a 250 ml of 3-necked flask, 4-(2,3-dimethylphenyl) phthalic acid (16 g, 48.5 mmol) was added, then potassium hydroxide (5.4 g, 97 mmol) in 60 ml of water was added. The reaction mixture was warmed to 80° C. and then potassium permanganate, KMnO$_4$ (~5 equiv.) was added as a solid in portion when the purple color disappeared periodically. The reaction mixture was allowed to proceed at 80° C. until the purple color of KMnO$_4$ persisted for 30 min. The excess KMnO$_4$ was killed by ethanol and the precipitated MnO$_2$ was filtered off. The solvent was evaporated to dryness and the resulting residue was acidified to PhH=1. The aqueous acidic solution as cooled in the refrigerator to induce crystallization. The solid was collected and dried to afford the desired product.

Synthesis of 2,3,3',4'-Biphenyldianhydride (6)

2,3,3',4'-Biphenyltetracarboxylic acid (4) (33 gm, 100 mmol) was suspended in minimum amount of acetic anhydride and heated to reflux for 4 hours. The reaction mixture was cooled to room temperature. The corresponding dianhydride precipitated out and was collected and washed with ether to remove trace of acetic acid before drying under vacuum to afford 26.5 g (90%) of a-BPDA. Mp=195-196° C.

Synthesis of Asymmetrical 2,3,3',4'-Biphenyl Dianhydride (a-BPDA)

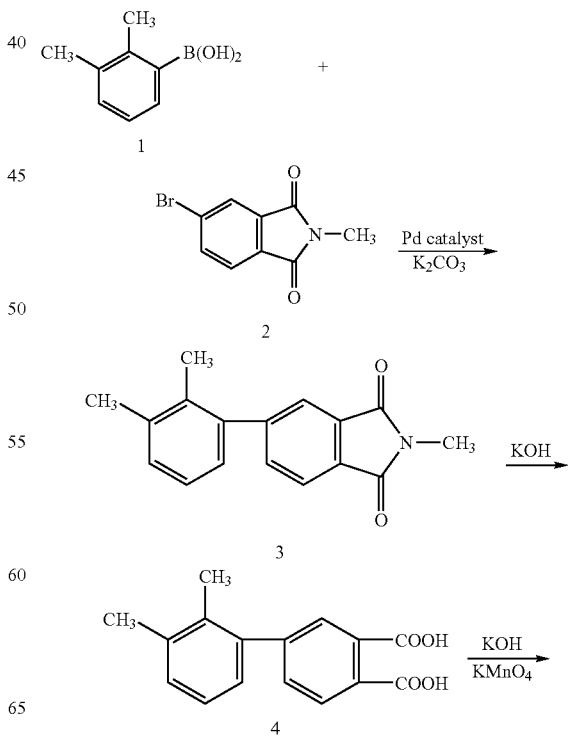

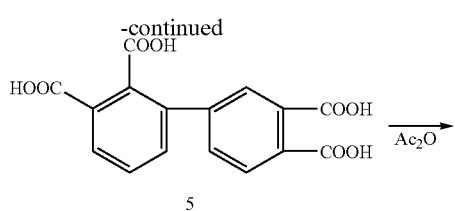

5

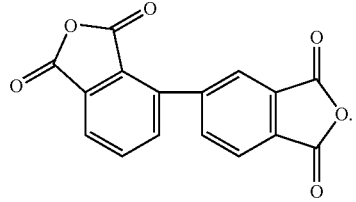

6
a-BPDA

The dianhydrides prepared by the processes of this invention are particularly useful in preparing polyimides from one or more of a combination of reactants comprising dianhydrides selected from the group consisting of 2,3,3',4'-biphenyldianhydride (a-BPDA), 2,3,3',4'-benzophenone dianhydride (a-BTDA), and 3,4'-methylenediphthalic anhydride (a-MDPA), with at least one diamine and an endcap that can be melt-processed at temperatures between 232-270° C. (450-520° F.), without any solvent. The imide oligomers from this reaction have low-melt viscosities of 1-60 poise at 260-280° C. These imide oligomers are amenable to TRM, VARTM or resin infusion processes at 260-280° C. to product high quality polymer composites comprising carbon, glass, quartz or synthetic fibers for use at temperatures ranging up to about 550° to 650° F.

An example of preparing the oligomers and polyimides using the asymmetric dianhydrides prepared by the processes of this invention is illustrated by the following reaction:

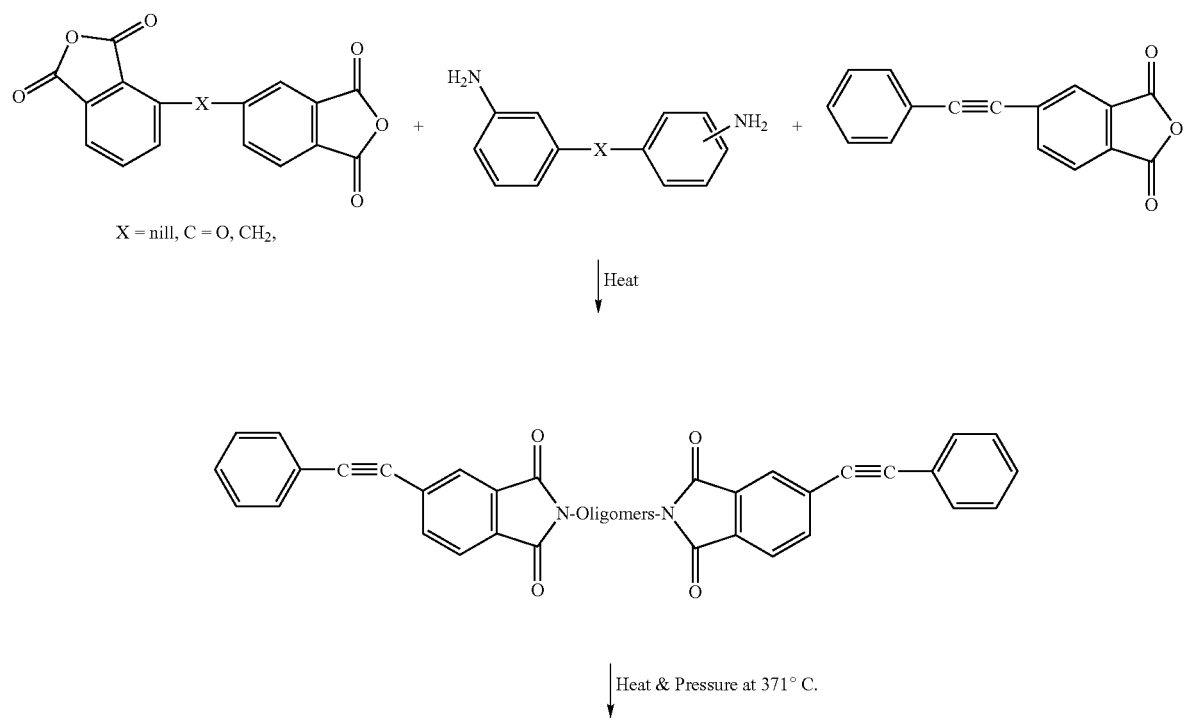

Thermoset Polyimide Resin

The invention claimed is:

1. Process for preparing asymmetrical tetracarboxylic acids which comprises cross-coupling a compound selected from the group consisting of:

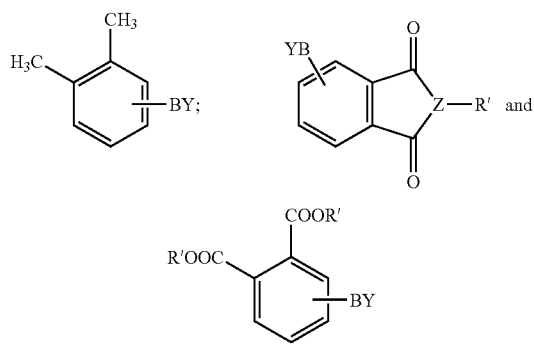

with a compound selected from the group consisting of

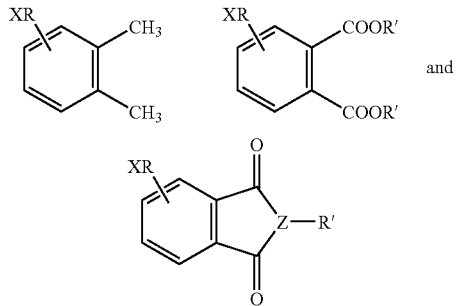

in the presence of catalysts and additives to obtain a coupled intermediate having a formula selected from the group consisting of:

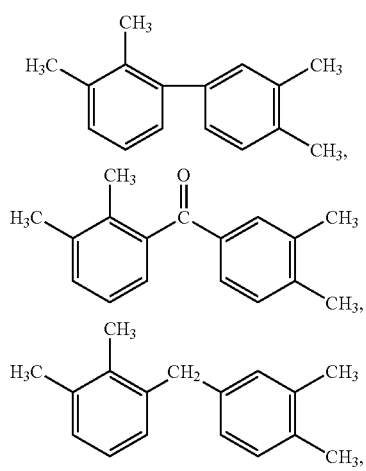

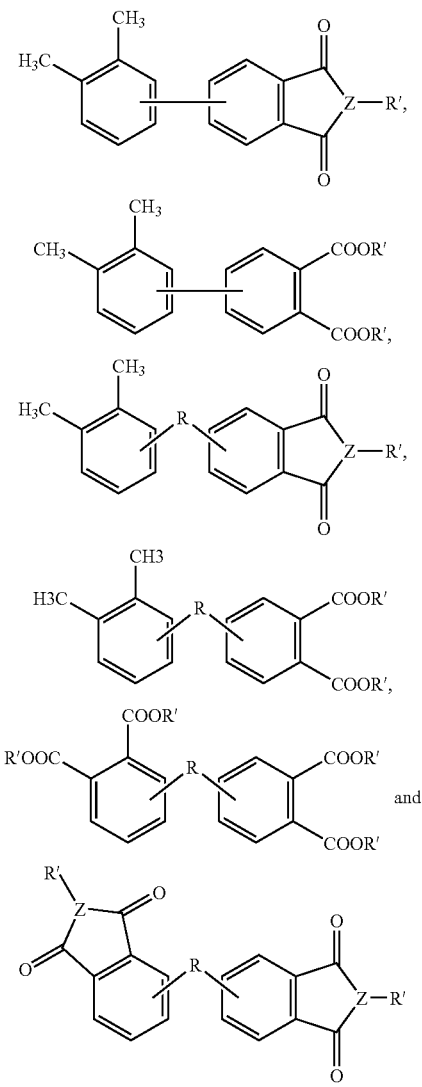

wherein R is nil, $CH_2$ or $C=O$, R' is a low alkyl group, Y is $(OH)_2$ or $(OR')_2$, Z is oxygen or nitrogen, X is selected from the group consisting of a halogen, $OSO_2CF_3$, and $OSO_2CH_3$, and B is boron; subsequently converting said intermediate to obtain tetracarboxylic acid selected from the group consisting of:

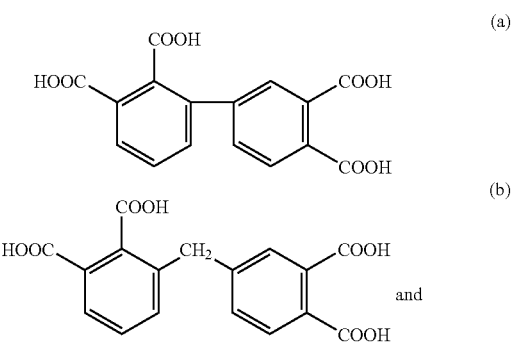

-continued (c)

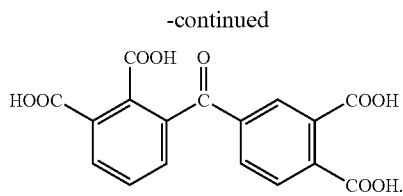

2. The process of claim 1 wherein palladium or nickel catalysts are present in the cross-coupling reaction.

3. The process of claim 1 wherein X is halogen and Y is $(OH)_2$, and the catalyst comprises palladium or nickel compounds.

4. The process of claim 1 wherein X is halogen, Y is $(OR')_2$, and the catalyst comprises palladium or nickel compounds.

5. The process of claim 1 wherein the 2,3,3',4'-biphenyl tetracarboxylic acid (a) is converted by dehydration into the corresponding 2,3,3',4'-biphenyl dianhydride having the formula:

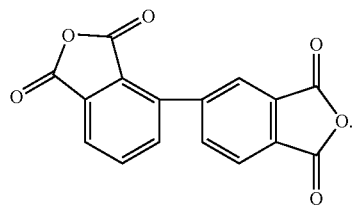

6. The process of claim 1 wherein the 2,3,3',4'-biphenyl tetracarboxylic acid is converted to 2,3,3',4'-biphenyl dianhydride by dehydration with acetic anhydride.

7. The process of claim 1 wherein 3,4'-methylenediphthalic acid (b) is converted by dehydration into the corresponding 3,4'-methylene diphthalic anhydride having the formula:

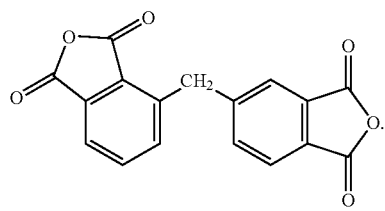

8. The process of claim 1 wherein the 2,3,3',4'-benzophenone tetracarboxylic acid (c) is converted by dehydration into the corresponding 2,3,3',4'-benzophenone dianhydride having the formula:

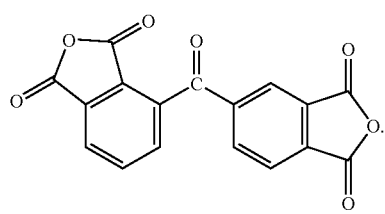

9. The process of claim 1 wherein the substituted compound has the formula:

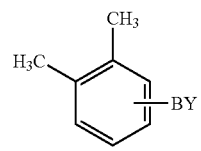

coupled with a compound having the formula:

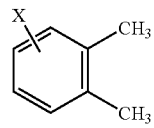

in the presence of catalysts to obtain the biphenyl intermediate having the formula:

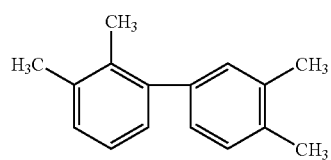

wherein R is nil, Y is $(OH)_2$, X is selected from the group consisting of a halogen, $OSO_2CF_3$ and $OSO_2CH_3$, and B is boron; said intermediate subsequently oxidized to the tetracarboxylic acid having the formula:

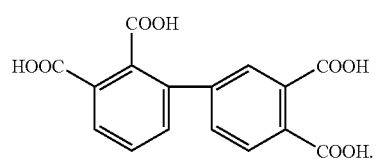

10. The process of claim 1 wherein the substituted compound has the formula:

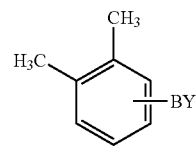

coupled with a phthalimide derivative having the formula:

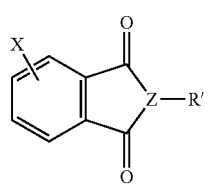

in the presence of catalysts to yield the biphenyl intermediate having the formula:

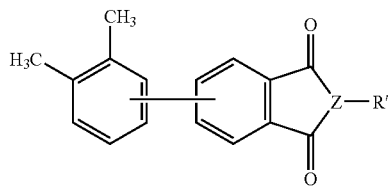

wherein R is nil, Y is (OH)$_2$, (OR')$_2$, X is selected from the group consisting of a halogen, OSO$_2$CF$_3$ and OSO$_2$CH$_3$, and B is boron, R' is lower alkyl group, Z is nitrogen;

said intermediate subsequently hydrolyzed and oxidized to obtain biphenyl tetracarboxylic acid having the formula:

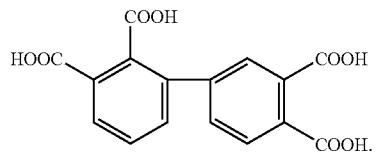

11. The process claim 1 wherein the substituted compound has the formula:

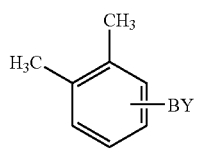

coupled with a phthalic ester to obtain compound having the formula:

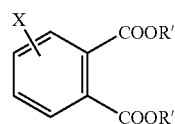

in the presence of catalyst to yield the biphenyl intermediate having the formula:

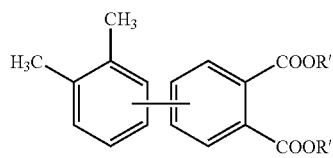

wherein R is nil, Y is (OH)$_2$ or (OR')$_2$, X is selected from the group consisting of a halogen, OSO$_2$CF$_3$ and OSO$_2$CH$_3$, and B is boron halogen, R' is lower alkyl group;

said intermediate subsequently hydrolyzed and oxidized to obtain the tetracarboxylic acid having the formula:

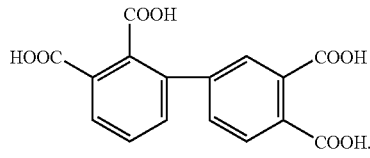

12. The process of claim 1 wherein a compound has the formula:

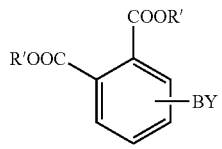

coupled with a compound having the formula:

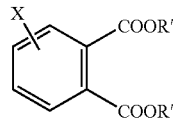

in the presence of catalysts to yield the biphenyl intermediate having the formula:

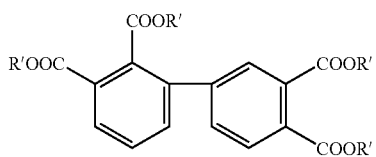

wherein B is boron, Y is (OH)$_2$, (OR')$_2$, X is selected from the group consisting of a halogen, OSO$_2$CF$_3$ and OSO$_2$CH$_3$, R' is lower alkyl group; said intermediate subsequently hydrolyzed to obtain the biphenyl tetracarboxylic acid having the formula:

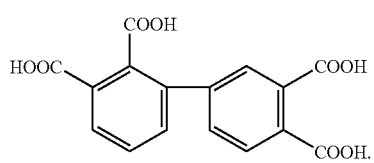

13. The process of claim 1 wherein a compound has the formula:

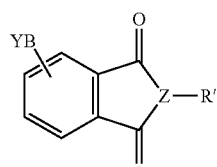

coupled with a compound having the formula:

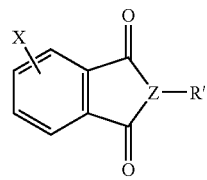

in the presence of catalysts to yield the biphenyl intermediate having the formula:

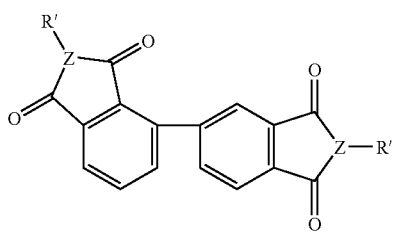

wherein R is nil, B is boron, Y is (OH)$_2$, (OR')$_2$, X is selected from the group consisting of a halogen, OSO$_2$CF$_3$ and OSO$_2$CH$_3$, Z is nitrogen or oxygen, R' is lower alkyl group; said intermediate subsequently hydrolyzed to obtain the biphenyl tetracarboxylic acid having the formula:

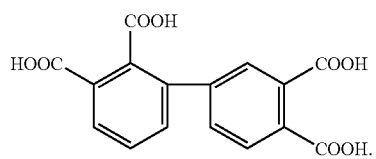

14. The process of claim 9 wherein 2,3,3',4'-biphenyl tetracarboxylic acid is converted by thermal or chemical dehydration to the corresponding 2,3,3',4'-biphenyl dianhydride (a-BPDA) having the formula:

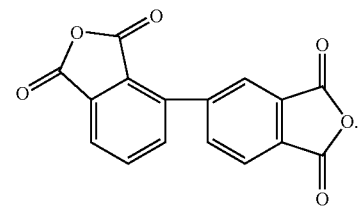

15. The process of claim 9 wherein the biphenyl tetracarboxylic acid is dehydrated with acetic anhydride to the corresponding biphenyl dianhydride.

16. The process claim 1 wherein, the substituted compound has the formula:

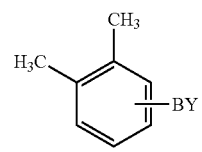

coupled with a compound having the formula:

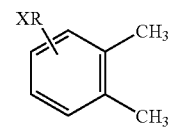

in the presence of catalysts to yield a intermediate having the formula:

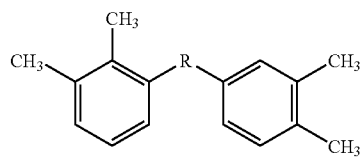

wherein R is CH$_2$ or C=O, X is selected from the group consisting of a halogen, OSO$_2$CF$_3$ and OSO$_2$CH$_3$, B is boron, Y is (OH)$_2$ or (OR')$_2$; said intermediate subsequently oxidized to obtain the tetracarboxylic acid having a formula:

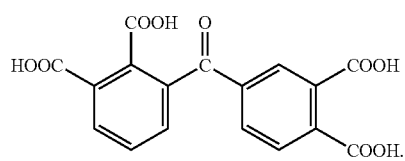

(C)

17. The process of claim 15 wherein the benzophenone tetracarboxylic acd (c) is reduced with hydrazine to 3,4'-methylenediphthalic acid having the formula:

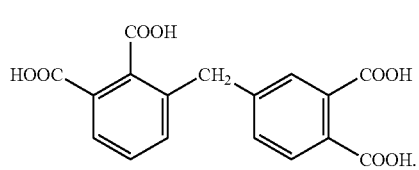

18. Process for preparing asymmetrical benzophenone tetracarboxylic acids which comprises cross-coupling with a compound having the formula:

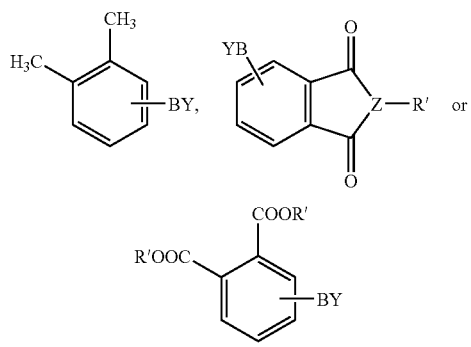

with a compound having the formula:

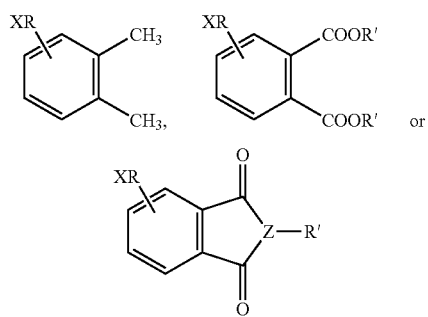

in the presence of catalysts and carbon monoxide when R is nil; but without carbon dioxide when R is C=O, to obtain benzophenone intermediates having a formula:

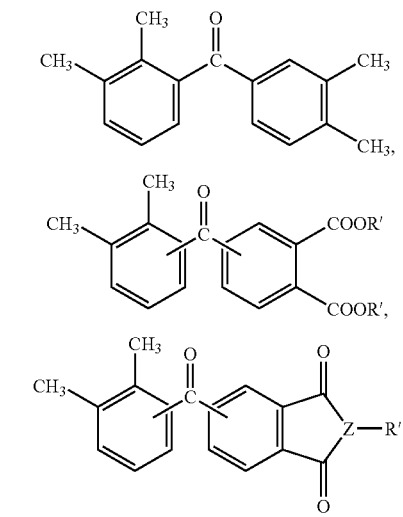

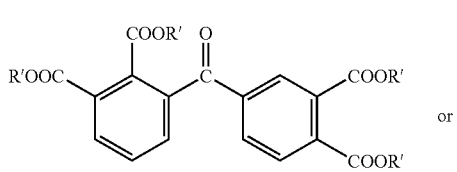

-continued

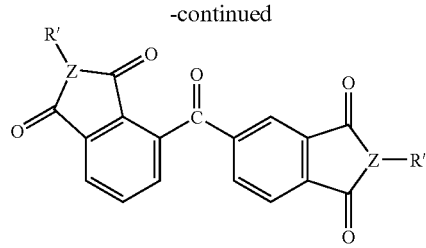

subsequently hydrolyzing and oxidizing said intermediate to obtain tetracarboxylic acid having the formula:

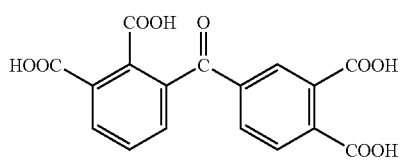

wherein R' is a low alkyl group, Y is $(OH)_2$ or $(OR')_2$, Z is oxygen or nitrogen, X is selected from the group consisting of a halogen, $OSO_2CH_3$, and B is boron.

19. The process claim 18 wherein the compound has the formula:

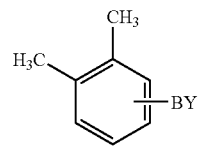

coupled in the presence of catalysts and carbon dioxide with a compound having the formula:

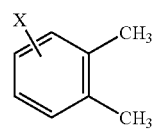

yields a coupled intermediate having the formula:

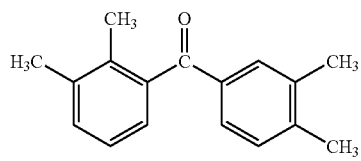

subsequent oxidized to obtain the tetracarboxylic acid having the formula:

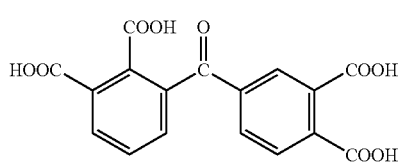

20. The process claim 18 wherein the compound has the formula:

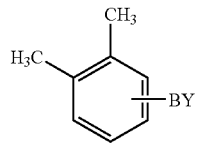

coupled in the presence of catalysts with a compound having the formula:

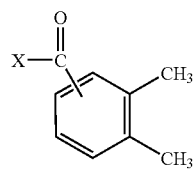

to obtain an coupled intermediate having a formula:

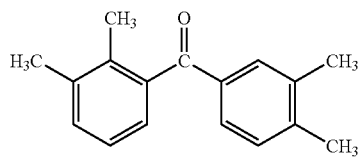

wherein B is boron, Y is (OH)$_2$, (OR')$_2$, X is halogen, R is C=O; said intermediate subsequently oxidized to afford benzophenone tetracarboxylic acid.

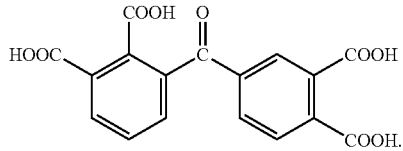

21. The process of claim 18 for preparing asymmetric tetracarboxylic acids which comprises cross-coupling a compound having the formula:

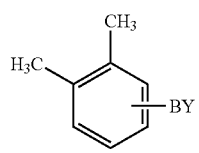

coupled with a substituted phthalic ester having the formula:

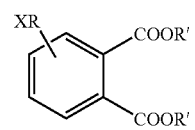

in the presence of catalysts to obtain an intermediate having the formula:

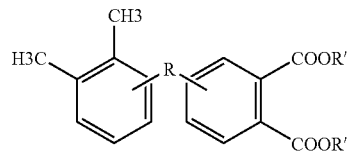

wherein R is CH$_2$, R' is a low alkyl group, Y is (OH)$_2$ or (OR')$_2$, X is selected from the group consisting of a halogen OSO$_2$CF$_3$, and OSO$_2$CH$_3$, and B is boron; said intermediate subsequently hydrolyzed and oxidized to obtain tetracarboxylic acid having the formula:

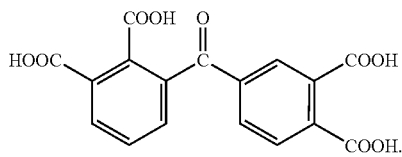

22. The process of claim 18 for preparing asymmetric tetracarboxylic acids which comprises cross-coupling a compound having the formula:

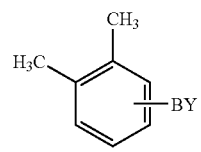

coupled with a substituted phthalimide having the formula:

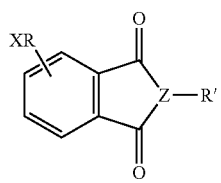

in the presence of catalysts to obtain intermediates having the formula:

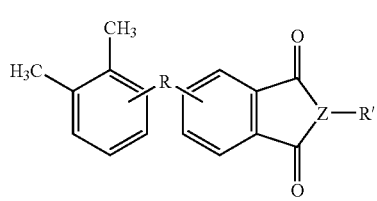

wherein R is CH$_2$, or C=O, R' is a low alkyl group, Y is (OH)$_2$ or (OR')$_2$, X is selected from the group consisting of a halogen, OSO$_2$CF$_3$, and OSO$_2$CH$_3$, and B is boron, Z is oxygen or nitrogen; said subsequently hydrolyzed and oxidized to obtain tetracarboxylic acid having the formula:

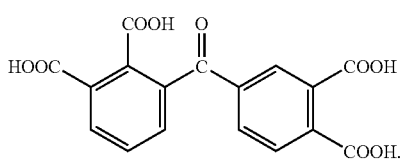

23. The process claim 18 wherein the 2,3,3',4'-tetracarboxylic acid is converted by dehydration into the corresponding 2,3,3',4'-benzophenone dianhydride having the formula:

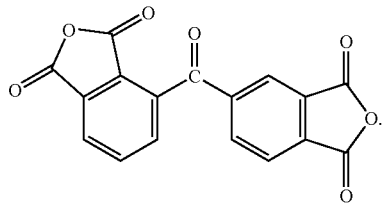

24. The process of claim 18 wherein the 2,3,3',4'-benzophenone tetracarboxylic acid is converted to 2,3,3',4'-benzophenone dianhydride by dehydration.

25. The process of claim 18 wherein 2,3,3',4'-benzophenone tetracarboxylic acid is converted to 2,3,3',4'-benzophenone dianhydride by dehydration with acetic anhydride.

26. The process of claim 18 wherein palladium or nickel catalysts are present in the cross-coupling reaction.

27. The process claim of 17 wherein the tetracarboxylic acid is converted by dehydration into the corresponding 3,4'-methylene diphthalic anhydride.

28. Process for preparing asymmetrical tetracarboxylic acids which comprises cross-coupling a substituted o-xylene having the formula:

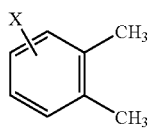

with a compound having the formula:

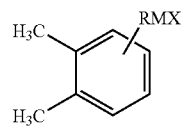

to produce an asymmetrical intermediate having the formula:

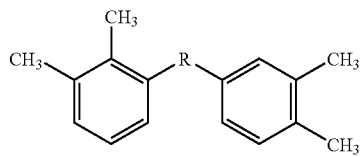

wherein X is halogen, R is nil, $CH_2$ or $C=O$, and M us a reactive metal, and subsequently oxidizing the said intermediate to produce the corresponding asymmetrical tetracarboxylic acid having the formula:

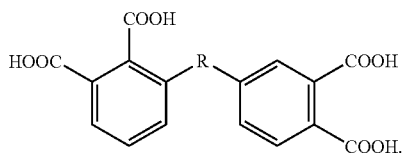

29. The process of claim 28 wherein the tetracarboxylic acid is converted by dehydration into the corresponding dianhydride having the formula:

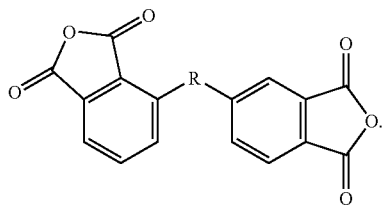

30. The process of claim 28 wherein M is a reactive metal selected from the group consisting of lithium, magnesium and zinc.

* * * * *